United States Patent
Sawaya

(10) Patent No.: US 8,530,449 B2
(45) Date of Patent: Sep. 10, 2013

(54) COMPOSITION FOR A TOPICAL OPHTHALMIC CLEAR COLLOIDAL LIQUID WHICH UNDERGOES A LIQUID-GEL PHASE TRANSITION IN THE EYE

(76) Inventor: Assad S. Sawaya, Baiting Hollow, NY (US)

( * ) Notice: Subject to any disclaimer, the term of this patent is extended or adjusted under 35 U.S.C. 154(b) by 0 days.

(21) Appl. No.: 12/807,637

(22) Filed: Sep. 9, 2010

(65) Prior Publication Data

US 2012/0064123 A1    Mar. 15, 2012

(51) Int. Cl.
*A61K 38/00* (2006.01)
*A61K 31/20* (2006.01)

(52) U.S. Cl.
USPC .............................. 514/54; 514/558; 514/912

(58) Field of Classification Search
USPC ........................................... 514/54, 558, 912
See application file for complete search history.

(56) References Cited

U.S. PATENT DOCUMENTS

| 6,261,547 B1 | 7/2001 | Bawa et al. |
| 2002/0035264 A1 | 3/2002 | Kararli et al. |
| 2004/0266725 A1 * | 12/2004 | Inohara et al. .................. 514/54 |

OTHER PUBLICATIONS

Derwent Abstract 200904, Aug 20, 2008.*

* cited by examiner

*Primary Examiner* — Zohreh Fay
(74) *Attorney, Agent, or Firm* — Dickstein Shapiro LLP

(57) ABSTRACT

The present invention is directed to a topical ophthalmic composition for a liquid comprised of clear colloidal polar nanolipids delivered in submicron sized particles (Nanopids™), aqueous colloidal lubricants, aqueous polymers, emulsifies, and a unique stabilizing buffer system, which undergoes a liquid-gel phase transition in the eye. Said composition is designed to deliver advanced eye lubricants, protect the three (3) layers of corneal film from dryness, and provide a unique system of Dry Eye treatment that addresses and treats all three layers of corneal tear film. Said composition is further designed to provide a superior delivery system of various Active Pharmaceutical Ingredients (APIs), and/or anti-infective/antibiotic/anti-fungal agents, accepted as safe and efficacious for ophthalmic use.

3 Claims, 2 Drawing Sheets

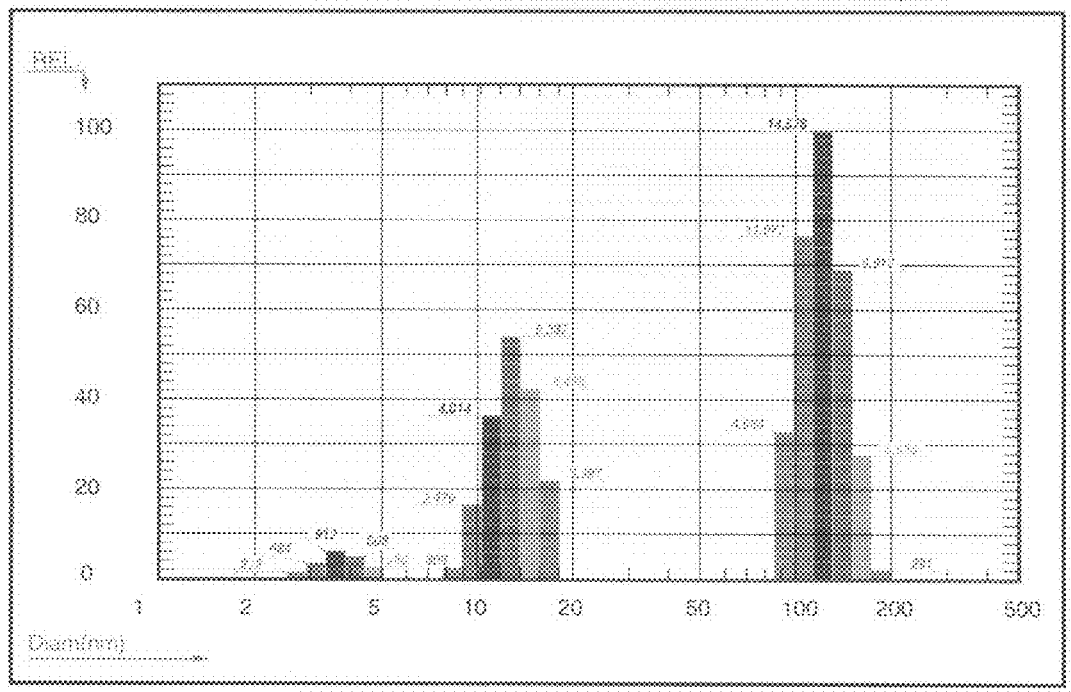

Figure 1 (#081810A): Ophthalmic Composition with Nanolipids, Aqueous Colloidal Lubricants, and Aqueous Polymers (Nano Particles) in a Buffered Liquid.

INTENSITY - Weighted NICOMP DISTRIBUTION Analysis (Solid Particle)
Count Rate 74 KHz Indicates a Substantial Count of Nanoparticles

| Peak 1- (Mean Diam 3.7 mm) | | Peak 2- (Mean Diam 13.1 mm) | | Peak 3- (Mean Diam 122.3 mm) | |
|---|---|---|---|---|---|
| mm | Count Rate | mm | Count Rate | mm | Count Rate |
| 3 | 228 | 8 | 309 | 100 | 4,664 |
| 3.5 | 664 | 10 | 2,470 | 120 | 11,077 |
| 4 | 912 | 12 | 4,014 | 140 | 14,576 |
| 4.5 | 608 | 14 | 8,337 | 160 | 9,912 |
| 5 | 380 | 16 | 6,465 | 180 | 5,655 |
|  |  | 18 | 3,397 | 200 | 291 |

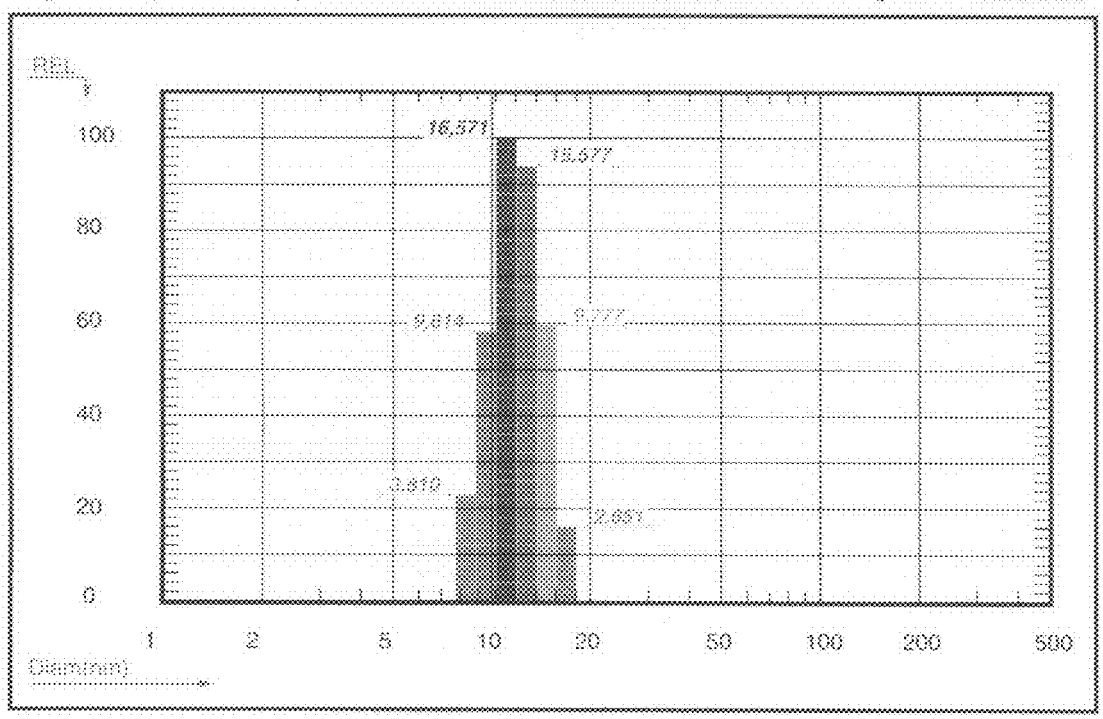

COMPOSITION FOR A TOPICAL OPHTHALMIC CLEAR COLLOIDAL LIQUID WHICH UNDERGOES A LIQUID-GEL PHASE TRANSITION IN THE EYE

BACKGROUND OF THE INVENTION

In healthy eyes, blinking induces the formation of tears which form a thin film which spreads over the corneal surface of the eye, making the surface smooth and optically clear, thereby enabling good vision. Said tear film is formed of three layers: an oil layer (lipids), a water (aqueous) layer, and a layer of mucus. The outermost layer is the lipid layer; its purpose is to smooth the tear surface and reduce evaporation of the eye's natural lubricants. The middle layer is the water layer; its purpose is to cleanse the eye and wash away any foreign particles or irritants. The innermost layer is the mucus layer; the mucus allows the water layer to spread evenly over the surface of the eye. Without the mucus layer, tears would not adhere to the eye.

Tears are produced by the Lacrimal Glands, located under the eyelids. "Dry Eye" is a condition caused by tear film instability and consequent ocular surface degeneration. Dry Eye may occur when the Lacrimal tear gland produces insufficient natural tears, in some instances as a normal consequence of the aging process during which lacrimal tissue may deteriorate and the lacrimal glands may shrink. Specifically, the lacrimal tissue may deteriorate and the lacrimal glands may shrink. Alternatively, dysfunction of the Meibomain gland may destabilize the tear film, or a blockage may occur in the execratory ducts of the lacrimal gland. Early signs and symptoms of Dry Eye include redness, burning, light sensitivity, gritty sensation, and watery eyes. As the normal base line tear production decreases, the eyes become dry and irritated. This may result in increased symptoms, including pain, redness blurred vision and infection. Over time, the reduced production of natural tears leads to dissipation of the lipid and mucous tear film layers. This in turn allows for evaporation of the aqueous layer, causing dry spots on the surface of the eye. The resulting impaired cellular surface leads to an unstable tear film, and a pathologically short tear break-up time (TBUT). If untreated, this condition will eventually exacerbate the symptoms noted above and result in ocular surface damage.

The present invention relates to a composition for a unique clear topical ophthalmic gel-forming liquid, delivering in a clear colloidal form for the first time submicron sized particles of clear colloidal oil droplets of polar nanolipids (Nanopids™), emulsifiers, and multiple aqueous tearlike ingredients (aqueous lubricants and/or aqueous polymers). The subject composition is uniquely designed to protect the three (3) layers of corneal film from dryness, deliver advanced eye lubricants, and to deliver a unique system of Dry Eye treatment that addresses and treats all three layers of corneal tear film. The size distribution of the clear colloidal polar lipids is in the range of 1.0 nanometers to 200.0 nanometers, with a preferred upper limit of 50 nanometers. The preferred mean average particle size is 13.0 nanometers (standard deviation of 3.2 nanometers) with a population distribution range of 6.0 nanometers to 22.0 nanometers. The size distribution of the aqueous colloidal particles is in the range of 3.0 nanometers to 200.0 nanometers. The preferred mean average particle size is 30.0 nanometers (standard deviation of 15.0 nanometers) with a particle size distribution range of 3 nanometers to 150 nanometers.

The subject composition also contains a unique gelling agent (anionic heteropolysachharide) which after introduction into the eye and upon contact with the cations naturally present in the pre-corneal tear film forms a clear gel. The composition allows the delivery of colloidal polar nanolipids in a clear gel form, and the additional benefits derived therefrom.

The clear (transparent) nature of the composition is a significant advantage of the invention. Conventional ophthalmic gel preparations, ophthalmic ointments and ophthalmic emulsions are uniformly cloudy or opaque. For example, the compositions of such conventional ophthalmic emulsions consist of large particle sizes that are generally greater than 1 micron, and can exceed 24 microns (e.g., Soothe.) When such conventional preparations are instilled in the eye, the result is prolonged blurred vision. Prolonged blurriness has a negative impact on patient acceptance of such ophthalmic preparations, and negatively impacts on patient compliance with the use of such products as directed. While adjustments in the viscosity of such conventional ophthalmic preparations may make the resultant formula less viscous, such will not resolve patient complaints of blurriness due to the cloudy/opaque nature of such preparations. In contrast, the clear nature of the subject composition will result in superior acceptance by patients, and a superior overall patient experience.

The present invention contemplates a unique clear ophthalmic gel-forming liquid designed to remedy the inability of Dry Eye patient's eyes to lubricate themselves through the natural replenishment of the tear film. The clear polar nanolipids play a major role in restoring and maintaining a healthy outer lipid layer of the tear film. The size, concentration and clarity of the colloidal polar nanolipids are particularly important for the subject composition. Conventional ophthalmic emulsions containing oil or lipids are cloudy due to the particle size. The particle size of these emulsions is greater than 1000 nanometers (greater than 1 micron). Some of these ophthalmic emulsions contain non-polar mineral oil with an oil droplet particle size greater than 10,000 nanometers (10 microns), in some cases with a particle size exceeding 24,000 nanometers (24 microns). Such formulations cause blurring in the eyes of users, negatively impacting on clarity of vision. Additionally, since they are non-viscous liquid emulsions, a large percentage of such preparations are blinked away during administration into the eye. As a result, only a small fraction of the dose remains in contact with the cornea. Conventional ophthalmic gel preparations and ophthalmic ointments present similar issues related to cloudiness and loss of the preparations due to their particle size. By contrast the subject composition containing the submicron sized nanoparticles, which in addition to allowing for the formation of a clear gel, results in a composition which is more effective in lubricating the eye and maintaining the tear film layers. First, the submicron sized particles of colloidal oil droplets of polar nanolipids comprising the subject composition are not lost as a result of blinking, resulting in prolonged eye exposure to the composition and any pharmaceutically active compounds present. Second, as the composition remains in colloidal liquid for until instilled into the eye, it is easier to administer to the eye, as compare to conventional ophthalmic emulsions, gel and/or ointment preparations.

The subject composition's formation of a clear viscous gel once administered into the eye further prolongs the delivery of nanolipids and nano-sized aqueous lubricants into the lacrimal fluid. As a result, the amount delivered is sustained over an extended time, providing a controlled bioavailability vehicle for delivery of the nanolipids and nano-sized aqueous lubricants to support the tear film. The subject colloidal liquid composition also contains a polysaccharide which undergoes a liquid-gel phase transition under the effect on an increase in cationic strength, and as such is diluted less rapidly which in turn provides for sustained delivery of the nanoparticles suspended in the subject composition. The prolonged exposure time provided by the subject composition results in delivery of a more effective concentration of the nanolipids and nanolubricants to the lacrimal fluid.

The dissipation of the lipid and mucous layers experienced by Dry Eye patients results in evaporation of the aqueous watery layer, causing dry spots. The resulting impaired ocular surface leads to an unstable tear film and a pathologic short tear break-up time (TBUT), which eventually results in ocular surface damage. Normal tear break-up time is approximately ten (10) seconds. A TBUT shorter than ten (10) seconds indicates a Dry Eye condition. If the tear film breaks up before a blink occurs, some portion of the eye will be exposed to desiccating elements. Through prolonged exposure to the air and environmental particulate matter, the unprotected ocular cells become desiccated and die. Eventually, the mucins will not be able to form a smooth ocular surface across the eye. As a result, the ability of the eye's naturally forming tears to adhere to the corneal epithelia is compromised, further shortening the tear break-up time and intensifying surface exposure.

A clinical study was performed on the composition that is the subject of the present invention (see Koch and Karpecki "Altaire Gel Forming Solution Study' referenced above at the 'Other Publications' section.) Clinical observation and testing of the composition as used by Dry Eye patients demonstrated a considerable improvement in the normal tear break-up time. The data showed a significant trend of increased tear break-up time, increasing from a 7.68 second TBUT baseline (prior to use of the subject invention) to 11.27 seconds after one (1) month of use of the composition. This measurable increase of over 3.5 seconds in TBUT is remarkable from a clinical perspective, since the duration of the study was only one (1) month and the composition was administered in a minimal dosage (2 times per day). Additionally, the composition significantly improved conjunctival staining after one (1) month of use. It also statistically improved 'Dry Eye' symptoms such as redness, dryness, headaches, feelings of grittiness or sandiness, scratchiness, and blurred vision. After installation of the subject composition such symptoms resolved in one (1) hour in eighty percent (80%) of the study subjects; a full one hundred percent (100%) of study subjects reported relief for thirty (30) minutes or more. This is a statistically significant improvement compared to the study baseline. Finally, the reported duration of the relief combined with the quality of vision results suggest that the subject composition provides a significant duration of relief of symptoms without compromising visual quality and acuity.

BRIEF SUMMARY OF THE INVENTION

The present invention is directed to a topical ophthalmic composition for a liquid comprised of clear colloidal polar nanolipids delivered in submicron sized particles (Nanopids™), aqueous colloidal lubricants, aqueous polymers, emulsifies, and a unique stabilizing buffer system, which undergoes a liquid-gel phase transition in the eye.

The present invention is also directed to methods of using these compositions for delivery of advanced eye lubricants, protecting the three (3) layers of corneal film from dryness, and a unique system to treat Dry Eye symptoms and conditions of Dry Eye treatment that address's and treats all three layers of the corneal tear film. Additionally, the subject composition is applicable as a delivery system for various pharmaceutically active compounds (Active Pharmaceutical Ingredients) recognized as safe and efficacious for the treatment of various ophthalmic conditions, diseases and/or disorders including but not limited to Dry Eye, Glaucoma, Ocular hypertension, infection, allergy, irritation, itching, redness and inflammation, and as a delivery system for anti-infectives, antibiotics, and combination anti-fungals, anti-virus and anti-inflammatory agents.

The composition is comprised of sub-micron sized colloidal polar lipids formed from one or more non-ionic polyethylene glycol derivatives of castor oil and/or hydrogenated castor oil (preferably Polyoxyl 35 Castor Oil), an anionic purified polysaccharide ('Gellan Gum'), one or more buffering agents (i.e. boric acid, trimethamine), one or more aqueous lubricants, and one or more colloidal aqueous lubricants.

The types of colloidal polar lipids that may be used in the present invention are polyethylene glycol derivatives of castor oil and polyethylene glycol derivatives of hydrogenated castor oil. As used herein, the term 'lipids' primarily refers to Polyoxyl 35 Castor Oil derived from castor oil, and it's equivalent Polyethylene Glycol derivatives of castor oil. The preferred lipid for the present invention is Polyoxyl 35 Castor Oil NF (a.k.a. Polyoxylethylenglyceroltricinoleat 35), trade names PEG 35 Castor Oil (Croda) or cremophor EL (BASF). When the Polyoxyl 35 Castor Oil is hydrated in an aqueous vehicle, colloidal polar nanolipids composed of sub-micron sized particles of oil droplets are formed as a clear colloidal liquid. In the present invention, the colloidal lipids formed from Polyoxyl 35 Castor Oil NF, after hydration with aqueous vehicles contain both a hydrophobic function group (i.e. "castor oil") and a hydrophilic function group (i.e. "PEG"). The hydrophobic group is non-polar, and having an affinity towards non-polar molecules, assists in the stabilization of the lipid layer of the tear film. Contrastingly, the hydrophilic group is polar, and has an affinity towards the aqueous layer of the tear film.

A variety of polyethylene glycol derivatives of castor oil and/or hydrogenated castor oil may be used for forming the colloidal particles. The scope of the present invention is not limited to Polyoxyl 35 Castor Oil NF/USP. Any and all forms/grades of polyethylene glycol derivatives of castor oils and/or hydrogenated castor oils, including but are not limited to those specified herein, may be used to form the colloidal particles. Examples include, but are not limited to, PEG-30 castor oil, PEG-33 castor oil, PEG-36 castor oil, PEG-40 castor oil, PEG-30 hydrogenated castor oil and PEG-40 hydrogenated castor oil. There are many polyethylene glycol derivatives of castor oil [hereinafter PEG castor oil] and polyethylene glycol derivatives of hydrogenated castor oil [hereinafter PEG Hydrogenated] available commercially that can be used to form the colloidal particles. This exemplification is non-exclusive.

The clear colloidal polar nanolipid particles are present in a size range of 1.0 nanometers to 200.0 nanometers, with a preferred upper limit of 50 nanometers, with a preferred mean average particle size of 13.0 nanometers (standard deviation of 3.2 nanometers) with a population distribution range of 6.0 nanometers to 22.0 nanometers. The content of polar lipid can be 0.1-15% w/v.

The present invention preferably is a composition comprised of Polyoxyl 35 castor oil in an ophthalmic liquid, which can contain a various amount of nanolipids. The size of such nanolipids particles is preferably within a narrow size range of 6.0 nanometers to 22.0 nanometers. Other sources of oils such as triglycerides and phospholipids can be emulsified to form hydrophobic/hydrophilic properties, and when hydrated will form colloidal particles. However, the size of such particles is too large and the resulting colloidal liquid is turbid rather than clear. The clarity of the colloidal liquid is dependant on the concentration and size range of the particles. Lipid colloidal particles that measure less than 50 nanometers will form clear colloidal liquids, while particles larger than 200 nanometers will form turbid liquids depending on concentration. The larger the particle size, the greater the turbidity.

The content of anionic polysaccharide is 0.05-2 w %, and it has a size of 3 to less than 100 nm, preferably 3-60 nm. Preferably, it has a mean size of 7.4-28.6 nm.

Gellan Gum (available for instance under the trade name "GelRite") is used as a gelling agent in culture medium and also in food products. Aqueous solutions containing about 0.05% to about 2.0% by weight of Gellan Gum are slightly viscous at low ionic strength (and non-viscous in absence of cations) but will undergo a liquid-gel transition when the ionic strength is increased. In the composition that is the subject of the present invention, such an increase in ionic strength occurs when the clear colloidal liquid is introduced into the eye. When ophthalmic liquid containing "Gellan Gum" is instilled into the eye, and upon contact with the cations present in the pre-corneal tear film, the viscosity of the liquid increases a gel is formed in the eye. After the composition undergoes this liquid-to-gel phase transition under the effect of an increase in cationic strength, said composition is diluted less rapidly in the eye than conventional ophthalmic solutions, and makes possible a sustained delivery of the nanoparticles suspended in said composition. This results in delivery of more effective levels of concentration of the nanolipids and nano-aqueous lubricants to the lacrimal fluid.

The composition that is the subject of the present invention may contain one or more aqueous polymers that are non-ionic. The polymers provide lubrication to the middle layer of the tear film. Said polymers are present in the subject composition in a clear colloidal form. The size of such colloidal polymers ranges from 3.0 nanometers to 150 nanometers.

The composition is buffered to a pH of 5-7.8, preferably 6.8-7.8. The buffering system allows use of the unique gelling agent in a clear topical ophthalmic liquid that is suitably stable and safe and efficacious for ophthalmic use. Boric Acid and tromethamine are preferably used in the buffering system of the composition that is the subject of the present invention. The buffering system used for the composition of the gel-forming colloidal liquid was deliberately formulated without cationic electrolytes, which is what works to prevent formation of a gel prior to the installation of the liquid composition into the eye. The buffering system as described herein allows for a stable base for the subject ophthalmic liquid composition by controlling the pH range, maintain the desired osmolality (250 to 400, preferably 280 to 330, mOsm/Kg.$H_2O$), eliminating the use of cations in the base, and preventing precipitation of any of the composition.

As noted above, the subject composition is a clear ophthalmic gel-forming liquid which, after introduction into the eye, forms a clear gel upon contact with the cations naturally present in the pre-corneal tear film. The clear (transparent) nature of the gel is a significant advantage of the invention. Conventional ophthalmic gel preparations, ophthalmic ointments and ophthalmic emulsions are uniformly cloudy or opaque. When such conventional preparations are instilled in the eye, the result is prolonged blurred vision. Prolonged blurriness negatively impacts both on patient acceptance of such ophthalmic preparations, and on patient compliance with the use of such products as directed. Adjustments in the viscosity of such conventional ophthalmic preparations will not resolve patient complaints of blurriness due to the cloudy/opaque nature of such preparations.

The present composition is a unique clear ophthalmic gel-forming liquid designed to remedy the inability of Dry Eye patient's eyes to lubricate itself through the natural replenishment of the tear film. The clear polar nanolipids (e.g., that sold under the name Nanopids™) play a major role in restoring and maintaining a healthy outer lipid layer of the tear film. The size, concentration and clarity of the colloidal polar nanolipids are particularly important for the subject composition. Conventional ophthalmic emulsions, gel preparations and ointments containing oil or lipids are cloudy due to their larger particle size. These formulations cause blurring in the eyes of users, negatively impacting on clarity of vision. Additionally, since they are non-viscous liquid emulsions, a large percentage of such preparations are blinked away during administration into the eye. As a result, only a small fraction of the dose remains in contact with the cornea. By contrast the subject composition containing the nanoparticles, which in addition to allowing for the formation of a clear gel, are more effective in lubricating the eye and maintaining the tear film layers. The submicron sized particles of colloidal oil droplets of polar nanolipids comprising the subject composition are not lost as a result of blinking.

The subject composition's formation of a clear viscous gel once administered into the eye results in a prolonged delivery of nanolipids and nano-sized aqueous lubricants into the lacrimal fluid that is sustained over an extended time, providing both a greater degree and longer duration of support to the tear film. The subject composition undergoes a liquid-gel phase transition and as such is diluted less rapidly, which in turn provides for sustained delivery of the nanoparticles suspended in the compositions. The prolonged exposure time provided by the subject composition results in delivery of a more effective concentration of the nanolipids and nano-lubricants to the lacrimal fluid.

BRIEF DESCRIPTION OF THE DRAWINGS

FIG. 1 (#081710D): Ophthalmic composition with nano-lipids (Nanopids™) containing PEG 35 Castor Oil. FIG. 1 illustrates the formation of the colloidal liquid. The particles represented are polar nanolipids. The mean diameter of such particles is 11.7 nanometers.

FIG. 2 (#081810A): Ophthalmic composition with nano-lipids (Nanopids™), aqueous colloidal lubricants, and aqueous polymers (nano particles) in a buffered liquid. FIG. 2 illustrates the formation of the three peaks of colloidal particles that make up the subject composition. The mean diameter of peak 2 is 13.1 nanometers, which consists mostly of nanolipids. The mean diameter of peak 3 is 122.3 nanometers, which mainly consists of aqueous nanoparticles from Povidone K-30, Hydroxyethylcellulose, and Polyvinyl Alcohol.

DETAILED DESCRIPTION OF THE INVENTION

The present invention is directed to liquid ophthalmic gel-forming compositions which are comprised of sub-micron sized colloidal polar lipids formed from one or more non-ionic polyethylene glycol derivatives of castor oil and/or hydrogenated castor oil (e.g., Polyoxyl 35 Castor Oil), an anionic purified polysaccharide (e.g., 'Gellan Gum'), one or more buffering agents (i.e. boric acid, trimethylamine), and preferably one or more aqueous lubricants, and one or more colloidal aqueous lubricants. The present invention is also directed to methods of using these compositions for delivery of advanced eye lubricants, protection of the three (3) layers of corneal film from dryness, and delivery of a unique system of Dry Eye treatment that addresses and treats all three layers of corneal tear film, and as a delivery system for pharmaceutically active compounds (a.k.a. Active Pharmaceutical Ingredients) to treat various ophthalmic conditions, diseases and/or disorders including but not limited to Dry Eye, Glaucoma, Ocular hypertension, infection, allergy, irritation, itching, redness and inflammation.

The types of colloidal polar lipids that may be used in the present invention are polyethylene glycol derivatives of castor oil and polyethylene glycol derivatives of hydrogenated castor oil. PEG castor oil and PEG hydrogenated castor oil are predominantly glyceryl tricinoleyl polyethylene glycols and tri-12-hydroxylstearyl polyethylene glycols, respectively. As used herein, the term 'lipids' primarily refers to Polyoxyl 35 Castor Oil derived from castor oil, and it's equivalent Polyethylene Glycol derivatives of castor oil. Castor oil is obtained by the pressing of seeds of the ricinus communis plant followed by heat clarification of the oil.

Many sources of lipids can be used in the present invention, such as triglycerides or soybean phospholipid (a.k.a. "soy lecithin.") The preferred lipid for the present invention is Polyoxyl 35 Castor Oil NF (a.k.a. Polyoxylethylenglycerol-tricinoleat 35), also identified by the trade names PEG 35 Castor Oil (manufactured by Croda) or cremophor EL (manufactured by BASF). Polyoxyl 35 Castor Oil NF contains mainly the tri-ricinoleate ester of ethoxylated glycerol, with small amounts of polyethylene glycol ricinoleate and the corresponding free glycols. It results from the reaction of glycerol ricinoleate with about thirty-five (35) moles of ethylene oxide. The hydrophobic part of Polyoxyl 35 Castor Oil are glycerol-polyethylene glycol ricinoleate together with fatty acid esters of polyethylene glycol and some uncharged castor oil. The smaller hydrophilic part of Polyoxyl 35 Castor Oil are polyethylene glycols and ethoxylated glycols. The hydrophobic part is about 83% while the hydrophilic part is about 17%. Polyoxyl 35 castor oil is a non-ionic surfactant, the functional group causes ricinoleic acid (and castor oil) to be unusually polar and allows chemical derivatization that is not practical in most other seed oils. In the present invention, the colloidal lipids formed from Polyoxyl 35 Castor Oil NF, after hydration with aqueous vehicles contain both a hydrophobic function group (i.e. "castor oil") and a hydrophilic function group (i.e. "PEG"). The hydrophobic group is non-polar, and having an affinity towards non-polar molecules, assists in the stabilization of the lipid layer of the tear film. Contrastingly, the hydrophilic group is polar, and has an affinity towards the aqueous layer of the tear film.

A variety of polyethylene glycol derivatives of (hydrogenated) castor oil may be used for forming the colloidal particles. The scope of the present invention is not limited Polyoxyl 35 Castor Oil NF/USP. Any and all forms/grades of polyethylene glycol derivatives of castor oils and/or hydrogenated castor oils, including but are not limited to those specified herein, may be used to form the colloidal particles. Examples include, but are not limited to, PEG-30 castor oil, PEG-33 castor oil, PEG-36 castor oil, PEG-40 castor oil, PEG-30 hydrogenated castor oil and PEG-40 hydrogenated castor oil. There are many polyethylene glycol derivatives of castor oil [hereinafter PEG castor oil] and polyethylene glycol derivatives of hydrogenated castor oil [hereinafter PEG Hydrogenated] available commercially that can be used to form the colloidal particles.

The clear colloidal polar nanolipid particles are present in a size range of 1.0 nanometers to 200.0 nanometers, with a preferred upper limit of 50 nanometers, with a preferred mean average particle size of 13.0 nanometers (standard deviation of 3.2 nanometers) with a population distribution range of 6.0 nanometers to 22.0 nanometers.

When the Polyoxyl 35 Castor Oil is hydrated in an aqueous vehicle, colloidal polar nanolipids composed of sub-micron sized particles of oil droplets are formed as a clear colloidal liquid. The size of such nanolipids particles is preferably within a narrow size range of 6.0 nanometers to 22.0 nanometers. The present invention is a composition comprised of Polyoxyl 35 castor oil in an ophthalmic liquid, which can contain various amounts of nanoliquids. The amount of Polyoxyl 35 castor oil (polar lipid) can be 0.1% to 15% weight-by-volume.

Other sources of oils such as triglycerides and phospholipids can be emulsified to form hydrophobic/hydrophilic properties, and when hydrated will form colloidal particles. However, the size of such particles is too large and the resulting colloidal liquid is turbid rather than clear. The clarity of the colloidal liquid is dependant on the concentration and size range of the particles. Lipid colloidal particles that measure less than 50 nanometers will form clear colloidal liquids, while particles larger than 200 nanometers will form turbid liquids depending on concentration. The larger the particle size, the greater the turbidity.

Colloidal polar lipids can be formed by emulsification of soy lecithin "phospholids" with Polysorbate 80. After hydration in an aqueous vehicle, the amount that can be emulsified and still result in a clear colloidal liquid is small. When 0.05% of soy lecithin is emulsified with 4% Polysorbate 80 and then hydrated to 100 mL of Purified Water, a clear colloidal liquid of nanolipids is formed. However, when 0.05% of soy lecithin is emulsified with 3% or less of Polysorbate 80 and then hydrated to 100 mL of Purified Water, a turbid colloidal liquid is formed. Turbid colloidal liquids are not suitable for an ophthalmic composition.

Triglycerides (e.g., those sold under the trade names "Neobee M-5" and "Neobee 1053", manufactured by Stepen) when emulsified with Polysorbate 80 and then hydrated in a hydrophilic vehicle form an opaque/turbid and unstable emulsion. The size of the particle is too large. These emulsions are not suitable for an ophthalmic composition. However, when a small amount of triglycerides (0.1%) is emulsified in a Polyoxyl 35 Castor Oil and then hydrated in a hydrophilic vehicle, a clear colloidal nanolipid liquid composition is formed. The clear colloidal liquid composition contains both Castor Oil and triglcerides nanolipids.

Gellan Gum (trade name "GelRite", manufactured by Kelco and Co.) is used a gelling agent in culture medium and also in food products. The structure of this heteropolysaccharide consists of the following repeating unit

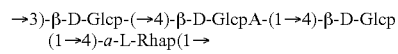

which may, or may not, be partially O-acetylated. Said structure is described as above in U.S. Pat. No. 4,326,053 (patent holder Merck and Co., Inc. Rahway, N.J.); said structure is also described in particular by Jansson and Linberg, Carbohydr. ROS. 124 35-9 (1983).

Aqueous solutions containing about 0.05% to about 2.0% by weight of Gellan Gum are slightly viscous at low ionic strength (and non-viscous in absence of cations) but undergo a liquid-gel transition when the ionic strength is increased. In the composition that is the subject of the present invention, such an increase in ionic strength occurs when the clear colloidal liquid is introduced into the eye. The rigidity of the gel can be modified by adjusting the polymer concentration. Additionally, when introduced into an aqueous solution Gellan Gum is both thixotropic and thermoplastic. These two properties enable its fluidity to be increased by shaking or slightly warming the sample before administration to the eye.

When ophthalmic liquid containing a purified non-ionic heteroploysacccharide "Gellan Gum" is instilled into the eye, and upon contact with the cations present in the pre-corneal tear film, the viscosity of the liquid increases and a gel is formed in the eye. Liquids containing 0.05% to approximately 2.0% by weight of "Gellan Gum" are non-viscous; where by design the liquid contains no cations, said liquid will undergo a liquid-to-gel transformation when the ionic strength (cations) is increased. In the instance of the composition which is the subject of the present invention, such an increase in the ionic strength of the ophthalmic aqueous liquid will occur when it is introduced into the eye, resulting in the forming of gel drops in the eye. After the colloidal liquid containing a polysaccharide undergoes liquid-to-gel phase transition under the effect of an increase in cationic strength, said composition is diluted less rapidly in the eye than conventional ophthalmic solutions, and makes possible a sustained delivery of the nanoparticles suspended in said composition. This process residence time permitted by the composition that is the subject of the present invention results in delivery of more effective levels of concentration of the nanolipids and nano-aqueous lubricants to the lacrimal fluid.

Boric Acid and tromethamine are used in the buffering system of the composition that is the subject of the present invention. The buffering system used for the composition of the gel-forming colloidal liquid was deliberately formulated without cationic electrolytes. The lack of cations in the product composition is what works to prevent formation of a gel prior to the installation of the liquid composition into the eye. The composition is buffered to a pH range of 5.0 to 7.8. The preferred pH range is 6.8 to 7.8. The concentration of boric acid ranges from approximately 0.1% to 10.0%. The concentration of trimethamine ranges from approximately 0.1% to 5.0%. The buffering system as described herein allows for a stable base for the subject ophthalmic liquid composition by controlling the pH range, maintaining the desired osmolality, eliminating the use of cations in the base, and preventing precipitation of any of the composition.

The composition that is the subject of the present invention may contain one or more aqueous polymers that are non-ionic, such as Polyvinyl Alcohol, Hydroxyethylcellulose and Povidone K-30 as well as propylene glycol, polyethylene glycol, sodium carboxymethylcellulose, and many others. The polymers provide lubrication to the middle layer of the tear film. Said polymers are present in the subject composition in a clear colloidal form. The size of such colloidal polymers range from 3.0 nanometers to 150 nanometers. The concentration of polyvinyl alcohol in composition that is the subject of the present invention ranges from 0.1% to 5.0%. The concentration of Hydroxyethylcellulose ranges from 0.1% to 1.0% and the concentration of Povidone K-30 ranges from 0.1% to 5.0%. Other non-ionic lubricants such as polysorbate 80, propylene glycol and glycerine also incorporated into the subject composition to provide lubrication to the middle aqueous layer of tear film. The concentration of polysorbate 80 ranges from 0.1% to 5.0%; the concentration of propylene glycol ranges from 0.1% to 2.0%, and the amount of Povidone K-30 ranges from 0.1% to 5.0%.

The application of the composition that is the subject of the present invention to a formulation also including various pharmaceutical active compounds is illustrated by the examples below. These include (A) Redness Relief: tetrahydrozoline HCl or naphazoline HCl, in a dose recognized as safe and efficacious for topical ophthalmic use, can be incorporated into the composition that is the subject of the present invention to provide redness relief.

(B) Allergy Relief: Addition of either ketotafen fumarate, olopatadine HCl, azelastine HCl, epinastine HCl, naphazoline HCl and pheniramine maleate, or lotpredenol etabonate to the composition that is the subject of the present invention will provide relief of better and a longer duration of relief allergy eye symptoms, including but not limited to the relief and prevention of itching associated with allergic conjunctivitis.

(C) Delivery Of Anti-Infectives, Antibiotics, And Combination Anti-Fungals, Anti-Virus And Anti-Inflammatory Agents: The following agents, in a dose recognized as safe and efficacious for topical ophthalmic use, could be incorporated into the composition that is the subject of the present invention: ciproflaxin HCl, gatifloxacin, gentamicin sulfate, gramicidin, erythromycin, levoflaxin, moxifloxacin HCl, natamycin, neomycin sulfate, ofloxacin, polymixin B sulfate, sodium sulfacetamide, tobramycin, trimethoprim sulfate, bacitracin, dexamethasone, flurometholone, hydrocortisone, prednisolone, tripfluridine, naproxen, diclofenac, surofen, keterolac, and tetrahydocortisol.

(D) Treatment Of Various Ophthalmic Conditions, Diseases And/Or Disorders Including But Not Limited To Dry Eye, Glaucoma, Ocular Hypertension, Infection, Allergy, Irritation, Itching, Redness And Inflammation: Dry Eye (including but not limited to cyclosporine and derivatives thereof), anti-hypertensive agents (para-aminoclonidine), anti-glaucoma agents (including but not limited to betaxolol, timolol maleate, pilocarpine HCl, carbonic anhydrase inhibitors, prostglandins), neuroprotective agents, dopaminergic antagonists, mucosecretagogue agents, angiostatic agents, proteins, growth factors (i.e. epidermal growth factor) and pain relievers, may be efficaciously treated by incorporation into the subject composition the pharmaceutically active ingredients/agents listed herein in dosages recognized as safe and efficacious.

(E) Delivery of Vitamin and/or Homeopathic Agents: the subject composition is also applicable to the delivery of vitamins and/or homeopathic preparations in a gel drop) into the eye for treatment of various ophthalmic conditions, diseases and/or disorders including but not limited to dry eye, glaucoma, ocular hypertension, infection, allergy, irritation, itching, redness and inflammation.

In summary, the composition is a uniquely designed composition of an ophthalmic liquid containing a clear gelling agent designed to deliver advanced eye lubricants, protect the three (3) layers of corneal film from dryness, and delivery of a unique system of dry eye treatment that addresses and treats all three layers of corneal tear film. The gelling agent is an anionic heteropolysaccharide. The ophthalmic composition contains clear colloidal polar nanolipids, and a stabilizing buffer system, and may also contain aqueous lubricants and/or aqueous polymers and emulsifiers, aqueous colloidal lubricants and an efficacious preservative system. The unique combination of the elements of the composition with the gelling agent in the stable buffering system results in a unique clear gel-forming ophthalmic liquid which delivers advanced eye lubricants, protects the three (3) layers of corneal film from dryness, and delivers multiple stages of dry eye treatment impacting on all three (3) layers of corneal tear film. Additionally, as noted above, the subject composition is also suitable for the efficacious delivery of various pharmaceutically active ingredients for the treatment of various of ophthalmic conditions.

EXAMPLE I

Topical ophthalmic composition containing nanolipids and other lubricants.

Phase I: compound amount (w/v) Gelrite 'Gellan Gum' 0.1%, polyvinyl alcohol 0.5%, hydroxyethylcellulose 0.3%, povidone K-30 2.0%, PEG 35 Castor Oil 1.0% and purified water q.s. to 80%. While mixing add the above items while maintaining a temperature of 85° C.±5° C. until completely dissolved. Transfer to a pressure tank and autoclave at 121.1° C. for 45 minutes, the cool down to 25° C.

Phase II: compound amount (w/v) of Boric Acid 1.12%, tromethamine 0.65%, Glycerine 0.5%, propylene glycol 0.3%, polysorbate 80 1.0%, sorbic acid 0.1% and purified water q.s. to 20%. Mix until dissolved. Aseptically filter the solution through a 0.2 micron filter into the sterile pressure tank containing phase I. Mix the entire batch for 30 minutes while maintaining the temperature at 25° C.

EXAMPLE II

Topical ophthalmic composition containing Naphazoline HCl

Phase I: compound amount (w/v) Gelrite 'Gellan Gum' 0.1%, polyvinyl alcohol 0.5%, hydroxyethylcellulose 0.3%, povidone K-30 2.0%, PEG 35 Castor Oil 1.0% and purified water q.s. to 80%. While mixing add the above items while maintaining a temperature of 85° C.±5° C. until completely dissolved. Transfer to a pressure tank and autoclave at 121.1° C. for 45 minutes, the cool down to 25° C.

Phase II: compound amount (w/v) of compound amount (w/v) of Boric Acid 1.12%, tromethamine 0.65%, Glycerine 0.5%, propylene glycol 0.3%, polysorbate 80 1.0%, Naphazoline HCl 0.03%, sorbic acid 0.1% and purified water q.s. to 20%. Mix until dissolved. Aseptically filter the solution through a 0.2 micron filter into the sterile pressure tank containing phase I. Mix the entire batch for 30 minutes while maintaining the temperature at 25° C.

EXAMPLE III

Topical ophthalmic composition containing Tetrahydrozoline HCl

Phase I: compound amount (w/v) Gelrite 'Gellan Gum' 0.1%, polyvinyl alcohol 0.5%, hydroxyethylcellulose 0.3%, povidone K-30 2.0%, PEG 35 Castor Oil 1.0% and purified water q.s. to 80%. While mixing add the above items while maintaining a temperature of 85° C.±5° C. until completely dissolved. Transfer to a pressure tank and autoclave at 121.1° C. for 45 minutes, the cool down to 25° C.

Phase II: compound amount (w/v) of compound amount (w/v) of Boric Acid 1.12%, tromethamine 0.65%, Glycerine 0.5%, propylene glycol 0.3%, polysorbate 80 1.0%, Tetrahydrozoline HCl 0.05%, sorbic acid 0.1% and purified water q.s. to 20%. Mix until dissolved. Aseptically filter the solution through a 0.2 micron filter into the sterile pressure tank containing phase I. Mix the entire batch for 30 minutes while maintaining the temperature at 25° C.

What is claimed is:

1. An ophthalmic liquid adapted for the treatment of dry eye consisting essentially of water, colloidal oil droplets containing clear nano-size polar lipid which is nonionic polyoxyethylated castor oil or nonionic polyoxyethylated hydrogenated castor oil having a particle size of 1-50 nm, and gellan, which is buffered to a pH of 5-7.8, is free of cationic electrolytes, and has an osmolality of 250-400 mOsm/kg.$H_2O$, said liquid being a clear liquid which forms a clear gel upon topical contact with the eye, and wherein said liquid is free of pharmaceutically acceptable active agent.

2. The ophthalmic liquid of claim 1 in which the composition is buffered to a pH of 6.8-7.8.

3. The ophthalmic liquid of claim 2 in which the polar lipid has a mean size of 9.8-16.2 nm, and the content of polar lipid is 0.1-15% w/v.

\* \* \* \* \*